United States Patent
Den Brinker et al.

(10) Patent No.: US 11,135,899 B2
(45) Date of Patent: Oct. 5, 2021

(54) DEVICE, SYSTEM AND METHOD FOR CO2 MONITORING

(71) Applicant: KONINKLIJKE PHILIPS N.V., Eindhoven (NL)

(72) Inventors: Albertus Cornelis Den Brinker, Eindhoven (NL); Vincent Jeanne, Migne Auxances (FR); Michel Jozef Agnes Asselman, Helmond (NL); Koray Karakaya, Eindhoven (NL); Gerrit Maria Kersten, Veldhoven (NL); Christian Andreas Tiemann, Eindhoven (NL); Murtaza Bulut, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 96 days.

(21) Appl. No.: 16/344,420

(22) PCT Filed: Oct. 27, 2017

(86) PCT No.: PCT/EP2017/077551
§ 371 (c)(1),
(2) Date: Apr. 24, 2019

(87) PCT Pub. No.: WO2018/083016
PCT Pub. Date: May 11, 2018

(65) Prior Publication Data
US 2020/0047582 A1 Feb. 13, 2020

(30) Foreign Application Priority Data
Nov. 2, 2016 (EP) .................................... 16196883

(51) Int. Cl.
*B60H 1/00* (2006.01)
*A61B 5/0205* (2006.01)
(Continued)

(52) U.S. Cl.
CPC ............ *B60H 1/008* (2013.01); *A61B 5/0205* (2013.01); *A61B 5/1118* (2013.01); *A61B 5/486* (2013.01);
(Continued)

(58) Field of Classification Search
CPC ........ A61B 2503/22; A61B 2560/0247; A61B 5/0077; A61B 5/0205; A61B 5/02405;
(Continued)

(56) References Cited

U.S. PATENT DOCUMENTS

| | | | | |
|---|---|---|---|---|
| 8,190,331 B2* | 5/2012 | Browne | ............. | B60H 1/00742 701/45 |
| 8,715,202 B2* | 5/2014 | Cardoso | ............... | A61B 5/0836 600/532 |

(Continued)

FOREIGN PATENT DOCUMENTS

| | | |
|---|---|---|
| CN | 2387422 Y | 7/2000 |
| CN | 104723843 A | 6/2015 |
| WO | 2013029738 A1 | 3/2013 |

OTHER PUBLICATIONS

Sechzer et al "Effect of CO2 Inhalation on Arterial Pressure, ECG and Plasma Catecholamines and 17-OH Corticosteroids in Normal Man" Journal of Applied Physiology, vol. 15, No. 3 May 1, 1960.
(Continued)

*Primary Examiner* — Babar Sarwar

(57) ABSTRACT

The present invention relates to a device, system and method for CO2 monitoring. To enable continuous monitoring at low cost and in a simple manner, the device comprises a signal input (10) for obtaining one or more monitoring signals (20) of a monitored area, a breathing monitor (11) for determining one or more breathing parameters (21) of one or more subjects present in the monitored area from the obtained one or more monitoring signals, and a CO2 esti-
(Continued)

mation unit (12) for estimating the CO2 level (22) in the monitored area based on the determined one or more breathing parameters.

14 Claims, 4 Drawing Sheets

(51) Int. Cl.
*A61B 5/11* (2006.01)
*A61B 5/00* (2006.01)
*A61B 5/024* (2006.01)
*A61B 5/08* (2006.01)
*A61B 5/083* (2006.01)
*A61B 5/091* (2006.01)

(52) U.S. Cl.
CPC ...... *B60H 1/00742* (2013.01); *A61B 5/02405* (2013.01); *A61B 5/0816* (2013.01); *A61B 5/0836* (2013.01); *A61B 5/091* (2013.01); *A61B 2560/0247* (2013.01)

(58) Field of Classification Search
CPC . A61B 5/02416; A61B 5/0816; A61B 5/0836; A61B 5/091; A61B 5/1118; A61B 5/486; A61B 5/681; B60H 1/00742; B60H 1/008; F24F 2110/70
See application file for complete search history.

(56) References Cited

U.S. PATENT DOCUMENTS

| | | | | |
|---|---|---|---|---|
| 9,227,484 | B1* | 1/2016 | Justice | B60H 1/00742 |
| 2005/0166760 | A1 | 8/2005 | Kim et al. | |
| 2007/0282227 | A1 | 12/2007 | Nanba et al. | |
| 2013/0006134 | A1* | 1/2013 | Doyle | A61M 16/0833 600/532 |
| 2013/0079658 | A1* | 3/2013 | Cardoso | A61B 5/0059 600/532 |
| 2013/0181836 | A1* | 7/2013 | Cardoso | G01M 15/108 340/540 |
| 2014/0275834 | A1* | 9/2014 | Bennett | A61B 5/6893 600/301 |
| 2014/0288447 | A1* | 9/2014 | Luna | A61B 5/0205 600/508 |
| 2014/0309864 | A1* | 10/2014 | Ricci | G01C 21/365 701/36 |
| 2015/0066311 | A1* | 3/2015 | Schroeder | G05D 3/00 701/49 |
| 2016/0103111 | A1* | 4/2016 | Griffin | B60N 2/002 73/25.01 |
| 2016/0302677 | A1* | 10/2016 | He | A61B 5/02125 |
| 2016/0318368 | A1* | 11/2016 | Alger | G01C 21/3453 |
| 2017/0080778 | A1* | 3/2017 | Suzuki | B60H 1/0075 |
| 2017/0190233 | A1* | 7/2017 | Wittliff, III | B60N 2/002 |
| 2018/0043901 | A1* | 2/2018 | Kim | A61B 5/024 |

OTHER PUBLICATIONS

Schaefer et al "Respiratory Acclimatization to Carbon Monoxide" U.S. Naval Medical Research Laboratory, Aug. 31, 1961.
Maskrey, M. et al., "The Respiratory Frequency Response to Carbon Dioxide Inhalation in Conscious Rabbits", University of Tasmania, Jun. 1979.
International Search Report and Written Opinion, International Application No. PCT/EP2017/077551, dated Feb. 8, 2018.
Philips Lighting, https://www.usa.lighting.philips.com/consumer, Accessed Apr. 2019.
Molecular Products Ltd., "Technical Article: A guide to breathing rates in confined environments", http://www.molecularproducts.com/pdf/technical-library/A%20Guide%20to%20Breathing%20Rates%20in%20Confined%20Environments%20Technical%20Article.pdf, Accessed Jul. 2016.
Bureau of Land Management, https://www.blm.gov/, Accessed Apr. 2019.
Biology Guide App, https://biologyguide.app/, Accessed Apr. 2019.
Whelan, R. et a., "The Effect of Adrenaline and Noradrenaline Infusions on Respiration in Man", Brit. J. Pharmacol., 1953.
Joels, N. et al., "The contribution of the arterial chemoreceptors to the stimulation of respiration by adrenaline and noradrenaline in the cat", J Physiol. Jul. 1968;197(1):1-23.
"Catecholamine", https://en.wikipedia.org/wiki/Catecholamine#Degradation, Accessed Apr. 2019.
Waters, M. et al., "Measurements of Indoor Air Quality on Commercial Transport Aircraft", National Institute for Occupational Safety and Health, Proceedings: Indoor Air 2002.
"Exposure Limits for Carbon Dioxide Gas", https://inspectapedia.com/hazmat/Carbon%20_Dioxide_Exposure_Limits.php, Accessed Apr. 2019.
Jung, H., "Modeling CO2 Concentrations in Vehicle Cabin", SAE International, Published Apr. 2013.

\* cited by examiner

DEVICE, SYSTEM AND METHOD FOR CO2 MONITORING

CROSS-REFERENCE TO PRIOR APPLICATIONS

This application is the U.S. National Phase application under 35 U.S.C. § 371 of International Application No. PCT/EP2017/077551, filed on 27 Oct. 2017, which claims the benefit of European Patent Application No. 16196883.9, filed on 2 Nov. 2016. These applications are hereby incorporated by reference herein.

FIELD OF THE INVENTION

The present invention relates to a device, system and method for CO2 monitoring. Further, the present invention relates to a vehicle comprising such a device.

BACKGROUND OF THE INVENTION

Normal dry air, at standard temperature and pressure (STP) of 101.325 kPa and 0° C., consists of (expressed in volume) 20.95 percent oxygen, 78.08 percent nitrogen, 0.0314 percent carbon dioxide, 0.93 percent argon and trace amounts of 14 other gases. Assuming that the oxygen content of the air is normal, the following figures are typical for confined rooms with very restricted airflow, such as underground mines:
  Normal air is 0.03% or 300 ppm CO2.
  The time-weighted threshold limit value for CO2 is 0.5% (or 5000 ppm).
  Headache and an increased rate of breathing occur at 10000 ppm (1%).
  The short-term exposure limit is 30000 ppm (3%), and these amounts result in doubling of normal breathing rate.
  Panting and intoxication occur above 50000 ppm (5%)
  Unconsciousness occurs above about 100000 ppm (10%).
  For daily living situations the following numbers are typical:
  If a person stays in a small bedroom and closes all windows/doors, the level will go towards 2000-3000 ppm after a couple of hours.
  In commercial transport aircraft cabins, the average CO2 concentration ranges are 515-4902 ppm, i.e. the higher boundary is very close to the threshold value of 5000 ppm. The recommended limit for continuous exposure is 1000 ppm.
  The CO2 concentration in vehicles very quickly reaches levels of 7000 ppm in recirculation mode. From example, for a vehicle with 3 passengers operating in full recirculation mode, it takes 50 minutes to reach 7000 ppm.

CO2 is twenty times more soluble in blood than oxygen. So the effect of CO2 level changes on the physiological parameters are much greater and faster when compared to the changes in O2 level of the air. Further, the effect of CO2 percentage increase first affects the breathing in a visible manner, and the heart rate changes only after higher levels are reached.

Assuming that CO2 levels are normal the following effects of the 02 changes are observed:
  The normal lower working limit for oxygen is 19%.
  At 18% oxygen there is a slight increase in breathing effort.
  At 16% triggers only a slight increase in heart and breathing rates.
  At 14%, emotional upset, impaired judgment and faulty co-ordination occur.
  At 12% cardiac damage and vomiting can occur.
  At 10%, a person would collapse into consciousness and death.

It has been found that for a person breathing at a rate of 12.5 liters per minute within a 'dead air' space of one cubic meter, an oxygen level of 18 percent will be reached at 58 minutes, whereas carbon dioxide levels will reach the threshold limit value of 0.5 percent at only 12 minutes, and the upper working limit of 1.25 percent at 30 minutes. This indicates that monitoring and eliminating the build-up of CO2 is much more critical than monitoring and preventing the drop in oxygen.

Decreased blood oxygen, increased CO2, and decreased pH level may result in the following physiological changes: A decrease of parasympathetic stimulation of heart, which increases the heart rate (HR), and an increase of sympathetic stimulation of the heart, which increases HR and strike volume, which increases vasoconstriction.

The CO2 level in air is not the only factor affecting the respiration rate and tidal volume (i.e. the depth of inhalation and exhalation). The response to a stressful experience leads to a changing concentration of catecholamines in the blood. An increasing concentration of epiphamine or nor-epiphamine leads to a respiration rate increasing rapidly (within a few minutes). Catecholamines have a half-life of a few minutes when circulating in the blood, as a result the respiration level will drop back to its baseline level within the order of minutes. In these cases, the heart rate will also change.

It should be noted that for certain patient groups (e.g. COPD) the sensitivity to CO2 level changes can be greater.

The obvious method to monitor the CO2 concentration level is using CO2 sensors, in which the most common type is non-dispersive infrared (NDIR) sensors. There are several limitations of this approach however: first, such sensors may be costly (although in recent years the price is dropping significantly), and second they are useful only for one function, namely for measuring the CO2 level.

SUMMARY OF THE INVENTION

It is an object of the present invention to provide a device, system and method for CO2 monitoring and particularly detecting an increase in CO2 volume at lower costs, wherein the device and system may preferably be usable for more than one purpose.

In a first aspect of the present invention a device for CO2 monitoring is presented comprising:
  a signal input configured to receive one or more monitoring signals of a monitored area, said monitoring signals being comprised in image data of the monitored area,
  a breathing monitor configured to determine one or more breathing parameters of one or more subjects present in the monitored area from the obtained one or more monitoring signals, and
  a CO2 estimation unit configured to estimate the CO2 level in the monitored area from a change in the determined one or more breathing parameters.

In a further aspect of the present invention a system for CO2 monitoring is presented comprising:
  a monitoring unit for acquiring one or more monitoring signals (20) of a monitored area, and a device as disclosed herein for CO2 monitoring based on the acquired one or more monitoring signals.

In a further aspect of the present invention a vehicle is presented comprising a device as disclosed herein for outputting one or more output signals for controlling a device of the vehicle and/or for recommending one or more actions to be taken.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, vehicle, computer program and medium have similar and/or identical preferred embodiments as the claimed device, in particular as defined in the dependent claims and as disclosed herein.

The present invention is based on the idea to monitor the physiological state, in particular the respiratory function, of one or more monitored subjects (i.e. persons), preferably with unobtrusive monitoring means such as a camera. Based on the monitored user parameters, the CO2 concentration changes can be estimated and appropriate actions may be taken or recommended to bring down the CO2 concentration to a normal level.

The proposed idea is particularly useful for monitoring the CO2 level in confined spaces. Such places include professional working environments such as mines and labs, and everyday places where air circulation can be limited or not, such as inside vehicles, and especially vehicles with multiple people.

According to an embodiment, the CO2 estimation unit is configured to estimate an increase in CO2 level when it observes positive change in at least one of breathing rate and breathing volume.

According to an embodiment, the breathing monitor is further configured to establish baseline breathing parameters by obtaining an average breathing rate over an initial period and wherein the CO2 estimation unit estimates the CO2 by comparison of the one or more breathing parameters to said baseline.

According to a preferred embodiment the device may further comprise an output signal generation unit for generating, in dependence on the estimated CO2 level, one or more output signals for controlling an external device and/or for recommending one or more actions to be taken and/or for information, and a signal output for outputting the one or more output signals. For instance, in a vehicle or room the air condition, the state of windows or doors, etc. may be controlled automatically, or recommendations may be issued for guiding the one or more subjects what to do to improve the CO2 level.

In another embodiment said output generation unit is configured to generate, as one or more output signals, one or more of a control signal for controlling or a recommendation to change the setting of a ventilation system, an air purifier, an air condition, one or more openings of a room, or a recommendation to change the location, or change the breathing, or minimize the physical activity. Generally, any external device may be controlled or any recommendation may be issued that may help to improve the CO2 level. Hereby, the designer or applicant of the system may implement certain control rules or recommendations based on the circumstances and the respective system elements that are available.

The signal input is preferably configured to obtain image data of the monitored area as monitoring signals and the breathing monitor is configured to determine said one or more breathing parameters from the obtained image data. For instance, motion of the belly or chest area may be detected in the image data (e.g. a time sequence of images or video data) to detect the respiration rate and/or respiration volume. Alternatively, the generally known photoplethysmography (PPG) technique may be used for this purpose. Methods for evaluating such motion or for using PPG for this purpose are generally known.

Various breathing parameters may hereby be used. The breathing monitor may thus be configured to determine, as breathing parameters, one or more of breathing rate, breathing depth, inspiratory time, expiratory time, inspiration to expiration time ratio, total breath time, fractional inspiration time, tidal volume, variability in one or more breathing parameters and changes of one or more breathing parameters over time.

In another embodiment said breathing monitor is configured to separately determine one or more breathing parameters for two or more subjects present in the monitored area and to identify changes of one or more breathing parameters for the two or more subjects separately. The CO2 estimation unit is then configured to estimate the absolute CO2 level based on the identified changes of one or more breathing parameters for the two or more subjects. Hence, by use of the present invention the breathing parameters for multiple persons can be determined separately, which can be used together for determining the CO2 level at an increased accuracy.

The breathing monitor may also be configured to identify changes of the one or more breathing parameters for the two or more subjects with respect to a baseline for the respective breathing parameter, in particular with respect to a common baseline for two or more subjects or with respect to individual baselines for one or more subjects. This further increases the CO2 level estimation.

In another embodiment the breathing monitor may be configured to identify changes of the breathing rate per subject and the CO2 estimation unit may be configured to determine, if the breathing rate and/or its change rate exceed a respective threshold for two or more subjects, that the CO2 level has exceeded a CO2 level threshold. This provides a simple but effective way of estimating the CO2 level.

The CO2 estimation unit may be configured to estimate the absolute CO2 level and/or changes of the CO2 level over time. This may provide further useful information for the user or the system, e.g. to decide if and which measures to take.

Preferably, the signal input is configured to obtain supplementary data including one or more of air quality data, environmental data, subject behavior data, and sensor data, wherein said breathing monitor is configured to identify changes of the one or more breathing parameters for an individual subject, in particular with respect to a baseline, from the obtained one or more monitoring signals and the obtained supplementary data. This leads to an increased accuracy of the CO2 level estimation.

The device may further comprise a heart rate monitor for determining heart rate of the one or more subjects, wherein the CO2 estimation unit is configured to estimate the CO2 level in the monitored area based on the determined one or more breathing parameters and the determined heart rate and/or changes of heart rate over time. This further increases the accuracy. Optical heart rate monitors are also able to estimate breathing rate from PPG signals. Hence, an optical heart rate monitor could be used to replace or supplement the above-mentioned breathing detection. For instance, a wrist-worn device, like a fitness monitor or health watch, may be used to detect heart rate and/or breathing rate.

The device may further comprise a motion detector for detecting physical motion of a subject, wherein said $CO_2$ estimation unit is configured to ignore breathing parameters of a subject determined during a phase of physical motion of said subject above a motion threshold or take said physical motion into account in the estimation of the $CO_2$ level.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
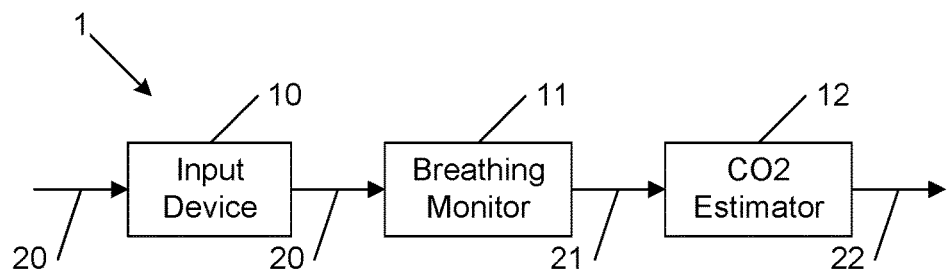
FIG. 1 shows a schematic diagram of a first embodiment of a device according to the present invention.

FIG. 1 shows a schematic diagram of a first embodiment of a device 1 according to the present invention. The device 1 comprises a signal input 10 for obtaining one or more monitoring signals 20 of a monitored area, a breathing monitor 11 for determining one or more breathing parameters 21 of one or more subjects present in the monitored area from the obtained one or more monitoring signals, and a $CO_2$ estimation unit 12 for estimating the $CO_2$ level 22 in the monitored area based on the determined one or more breathing parameters.

The device 1 may generally be implemented in hard- and/or software, e.g. as a processor, computer or application program ("app") running on a user device, such as a smartphone, that is programmed accordingly.

One main application of the present invention may be in vehicles, such as cars and buses. A car can be considered a confined environment, provided that the ventilation system of the car controls the fresh air intake (from outside). Nowadays cars are equipped with ventilation systems that can monitor the outside air pollution and based on its level can decide to prevent access to outside air, to allow the outside air to enter in. Obviously, the driver can also change these ventilation settings. Other possible applications might be waiting rooms or hospital rooms. $CO_2$ build-up is most common in enclosed spaces, though these do not need to be completely enclosed because $CO_2$ is slightly denser than air and tends to sit in pockets in still air. Therefore, the more common use areas might be in encloses or partially enclosed spaces but use may be possible in more open areas, though air movements there may often make it less useful.

The monitoring unit for acquiring the monitoring signal 20 may be a camera, such as a vital signs camera used in vital signs monitoring using PPG techniques, targeting the respiration monitoring in particular. In an embodiment the camera images are processed and a respiration signal is created. Using camera image further enables discrimination between users. Multiple users can be monitored with a single camera. In more detail, there are various techniques for monitoring and extracting the respiration or breathing signal. One possibility can be by detecting movement in the chest and/or abdoment using movement detection processing on the images. Clothing can cause problems for this method. Another technique is to form 1D projections of a selected region and correlating 1D projections from images obtained at different times. Another possibility is to use colour changes in the skin to extract a heart rate signal and detect changes in this which are caused by breathing. This technique requires exposed skin areas to be in the monitored area though this can be ensured by choosing the position of the camera.

From the respiration signal, respiration markers can be extracted. For instance, respiratory frequency, inspiratory time, expiratory time, inspiration to expiration time ratio, total breath time, tidal volume, fractional inspiration time, breath depth, variability of in the respiration parameters (frequency, intensity, timing parameters) are variables that can be derived from the respiratory signal. Some of these have clinical relevance especially for populations at risk such as COPD patients.

Alternatively, other monitoring units different from a vital signs camera, which are capable of monitoring one or more breathing parameters, can also be used for the same purpose.

In an embodiment, changes in the breathing rate and depth are observed. When many people are travelling together the risk of increased $CO_2$ level is greater, which case will be described in the following. First, a baseline breathing rate (and depth) of each person may be determined. Next, each passenger is continuously monitored with regard to the breathing rate changes. As explained above, air $CO_2$ volume increase causes breathing rate to increase. This is a reaction of the body, and individuals do not have control over it. Benefiting from this clear physiological reaction, the breathing rate changes for each person are detected, and when it is observed that the rate has increased and is continuing to increase for each person, an alert of high $CO_2$ volume in air is activated. A similar reaction is expected for each person in the car. Hereby, other effects influencing the breathing rate besides $CO_2$ can be cancelled out.

Figure 7A:
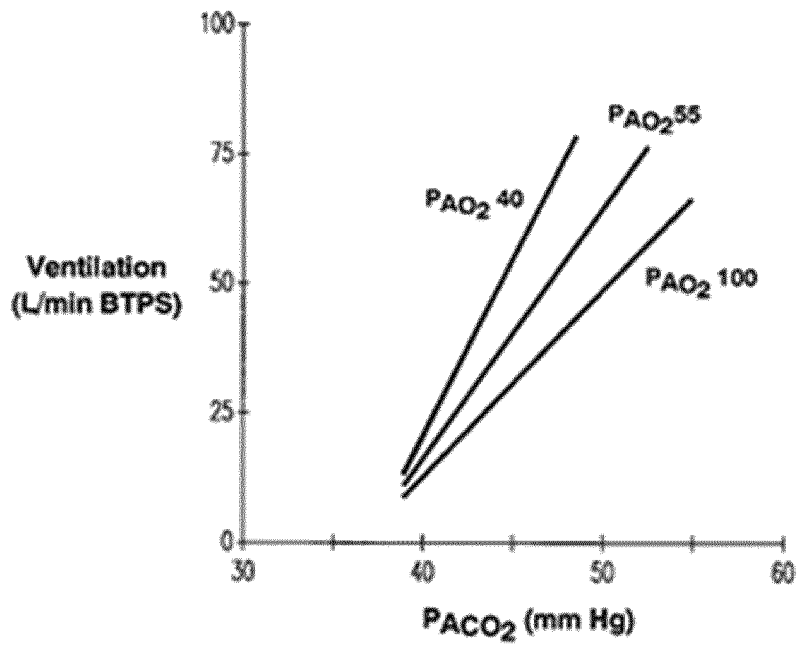
FIG. 7a illustrates a graph showing how the concentration of $CO_2$ is related to the breathing rate.
Figure 7B:
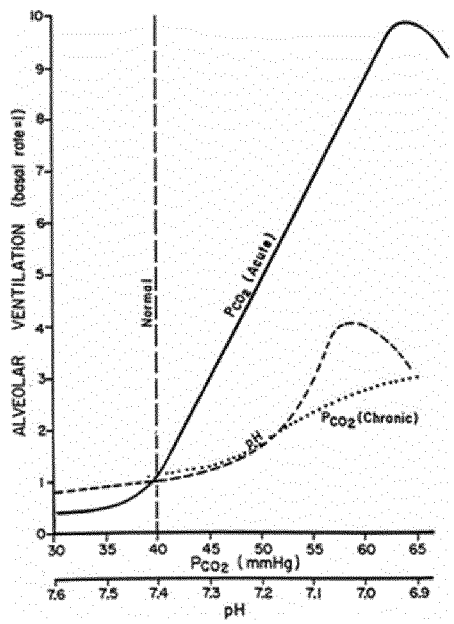
FIG. 7b illustrates a graph showing the increase in ventilation starts to occur very soon after there is an increase of $CO_2$ concentrations from normal levels.

FIGS. 7a and 7b (Caruana et al, "The Control of Breathing in Clinical Practice, CHEST 2000; 117; 20-225) show how the concentration of $CO_2$ is related to the breathing rate. FIG. 7a shows that the ventilation rate (measure in volume of air moved) increases proportionally to increased $CO_2$ concentration. From FIG. 7b, it can be seen that the increase in ventilation starts to occur very soon after there is an increase of $CO_2$ concentrations from normal levels and that the relationship is very close to linear until higher $CO_2$ levels are reached. Also it can be seen that a increase in $CO_2$ concentration from 40 to 60 mmHg causes a eight-fold increase in ventilation i.e. the constant of proportionality is 0.4. The ventilation or breathing rate is tidal volume multiplied by the frequency of breathing, the change of $CO_2$ concentration can be deduced from the change in these breathing parameters. Breathing depth is directly related to tidal volume and the breathing volume is, for a given person, related to the breathing amplitude. The breathing amplitude can be derived from the breathing signal.

Figure 2:
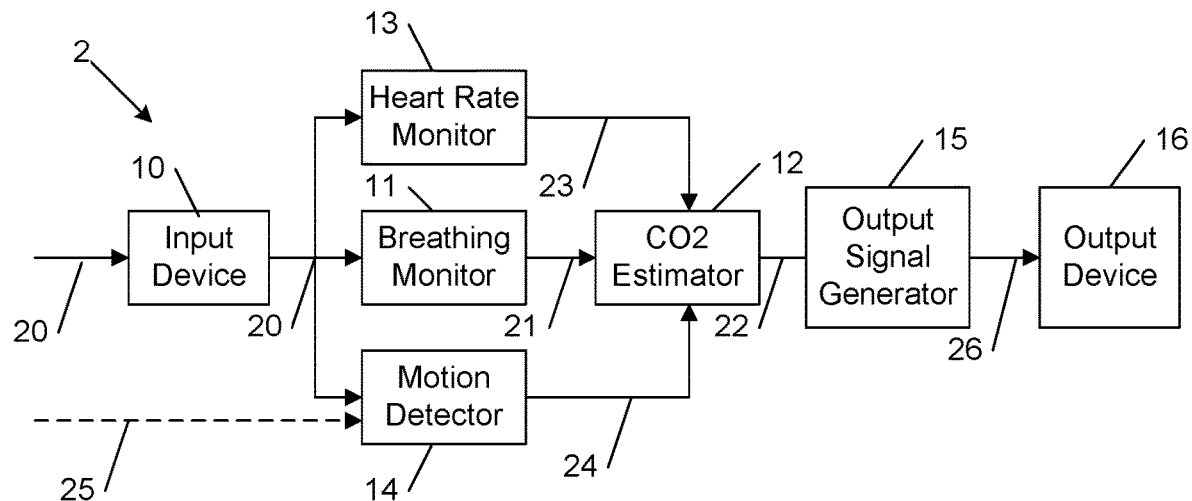
FIG. 2 shows a schematic diagram of a second embodiment of a device according to the present invention.

FIG. 2 shows a schematic diagram of a second embodiment of a device 2 according to the present invention. In this embodiment one or more further elements may be provided.

In one implementation the device 2 may further comprise a heart rate monitor 13 for determining heart rate 23 of the one or more subjects, wherein the $CO_2$ estimation unit 11 is configured to estimate the $CO_2$ level in the monitored area based on the determined one or more breathing parameters and the determined heart rate and/or changes of heart rate over time. The heart rate monitor 13 may be configured to detect the heart rate from the monitoring signals 20, e.g. by use of the PPG technique. Alternatively, other means for determining the heart rate may be provided, e.g. by use of a dedicated heart rate sensor, such as a pulse oximeter.

In another implementation the device 2 may further comprise a motion detector 14 for detecting physical motion 24 of a subject, wherein said $CO_2$ estimation unit 12 is configured to ignore breathing parameters of a subject determined during a phase of physical motion of said subject above a motion threshold or take said physical motion into account in the estimation of the $CO_2$ level. The motion detector 14 may be configured to detect the motion from the monitoring signals 20, e.g. by use of the PPG technique. Alternatively, other means for determining the motion may be provided, e.g. by use of a dedicated motion sensor, such as an accelerometer.

In another implementation the device 2 may further comprise an output signal generation unit 15 for generating, in dependence on the estimated $CO_2$ level, one or more output signals 26 for controlling an external device and/or for recommending one or more actions to be taken and/or for information, and a signal output 16 for outputting the one or more output signals 26. The signal output 16 may e.g. comprise a display and/or a loudspeaker for issuing a recommendation and/or an interface for issuing a control signal to an external device.

Thus, upon activation of an alert, the desire is to take actions to bring the air $CO_2$ volume back to normal levels. This can be done is multiple ways:

The setting of the vehicle ventilation system can change, so that more clear air is allowed to enter from outside, or the ventilation mode can be adjusted.

In case the outside air severely polluted, the driver can be instructed to take a different route, where the air is cleaner. In case of autonomous vehicles, the vehicle can adapt its route based on the observed changes in the respiration rate of the passengers.

If additional (external) devices such as air purifiers that can get rid of excess $CO_2$ are available, they can be activated.

Additionally, oxygen, oxygen enriched air, or clean air can be pumped in the environment.

The passengers can be instructed to minimize the physical activity and/or to breathe slowly.

Figure 3:
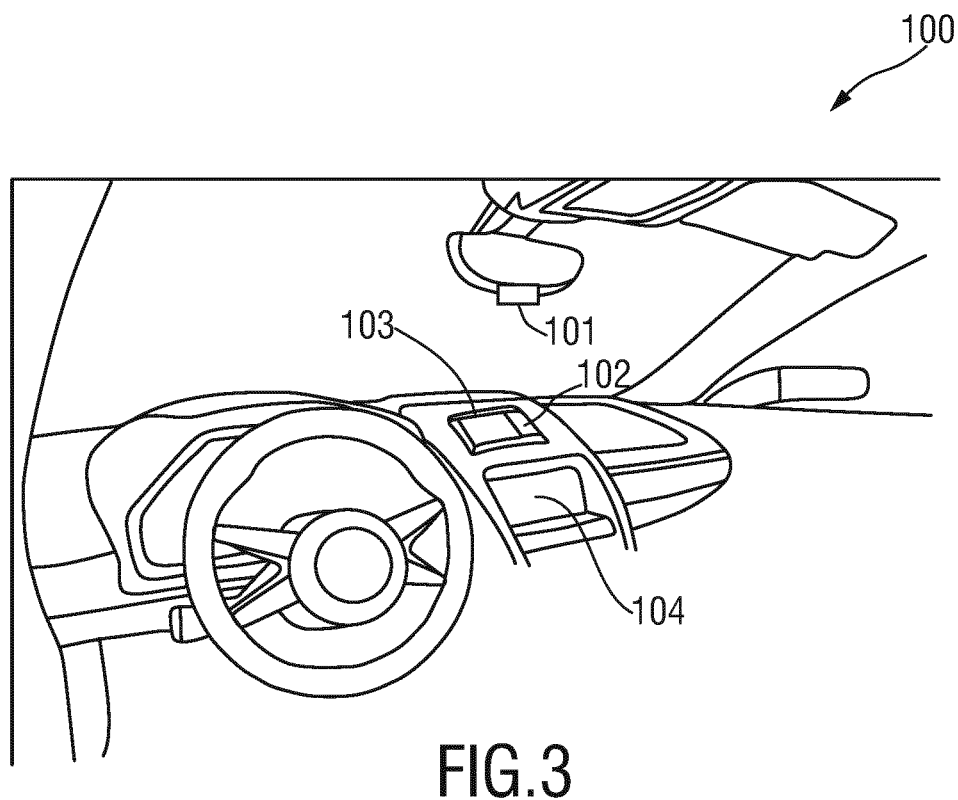
FIG. 3 shows a cockpit of a vehicle in accordance with an aspect of the present invention.

FIG. 3 shows a cockpit of a vehicle 100 in accordance with an aspect of the present invention. The vehicle, in this exemplary embodiment a car, represents an embodiment of the disclosed system and comprises a monitoring unit 101, such as a camera, a device 102 as disclosed herein for outputting one or more output signals for controlling a device 103, 104 of the vehicle and/or for recommending one or more actions to be taken. The device 103 may e.g. the air condition of the vehicle 100 and the device 104 may e.g. the monitor of the navigation system of the vehicle. Thus, the air condition 103 may be controlled automatically or a message may be issued on the monitor what the passengers should do (e.g. open the window).

Figure 4:
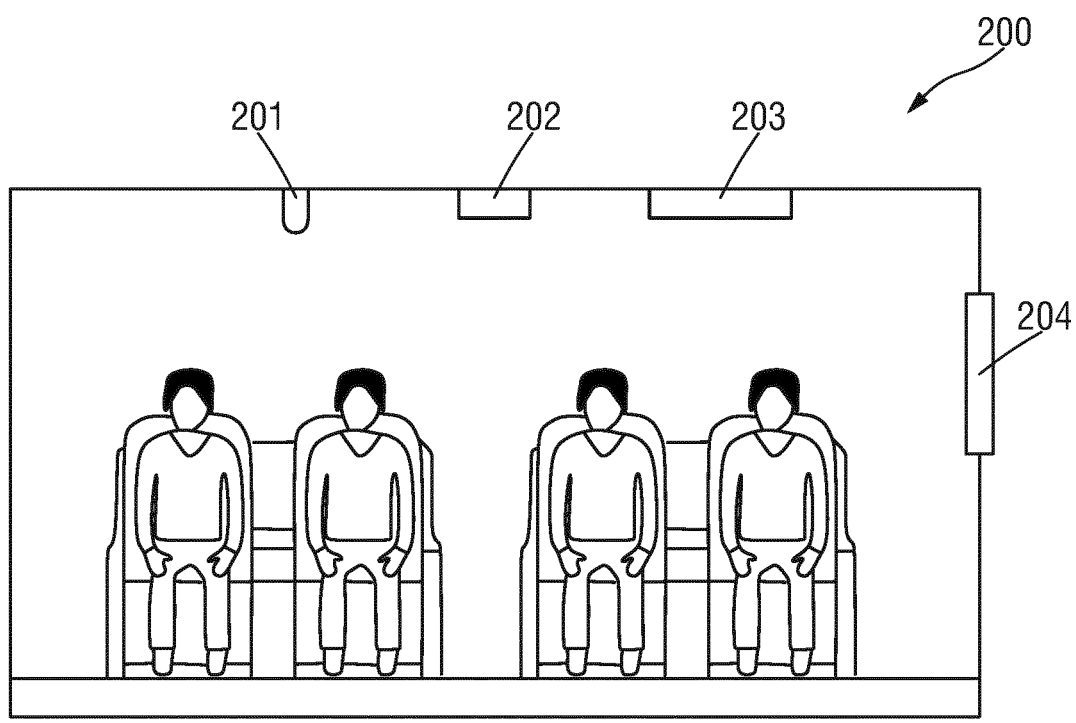
FIG. 4 shows a schematic diagram of an embodiment of a system in accordance with another aspect of the present invention.

FIG. 4 shows a schematic diagram of another embodiment of a system 200 in accordance with another aspect of the present invention. The system 200 is installed in this exemplary embodiment in a room, e.g. in a waiting room of an office building or a hospital. The system 200 comprises a monitoring unit 201, e.g. a camera, a device 202 as disclosed herein and two external devices 203, 204 that may be automatically controlled, such as the room's air condition 203 or a window 204.

A benefit of monitoring multiple persons is that the results can be averaged between those persons thereby reducing the effect of spurious results arising from changes in the breathing parameters of one person being caused by other factors than $CO_2$ levels.

Especially for people suffering from breathing problems (COPD, asthma), or people having problems with lungs and kidneys (the organs that compensate for pH imbalances) the proposed invention is of particular relevance. The ventilation setting in the car is designed having healthy people in mind. Similarly the settings of an air purifier are generally designed with healthy people in mind. This means that these settings may not be optimal for non-healthy people. Using the proposed approach, which enables real-time monitoring, the user health (in this case respiration) information can be fed-back to these devices (in a closed loop feedback system) and the operation of these devices can be adjusted accordingly.

Due to a stressful experience, the respiration rate can increase and decrease, however the time frame in which this takes place is in the order of minutes, after which the respiration rate will drop back to its baseline rate. Hence, by observing longer-term trends, the effect on respiration rate due to $CO_2$ can still be distinguished. Thus, in one embodiment the breathing monitor (11) is configured to identify changes of the one or more breathing parameters for two or more subjects with respect to a baseline for the respective breathing parameter, in particular with respect to a common baseline for two or more subjects or with respect to individual baselines for one or more subjects.

Figure 5:
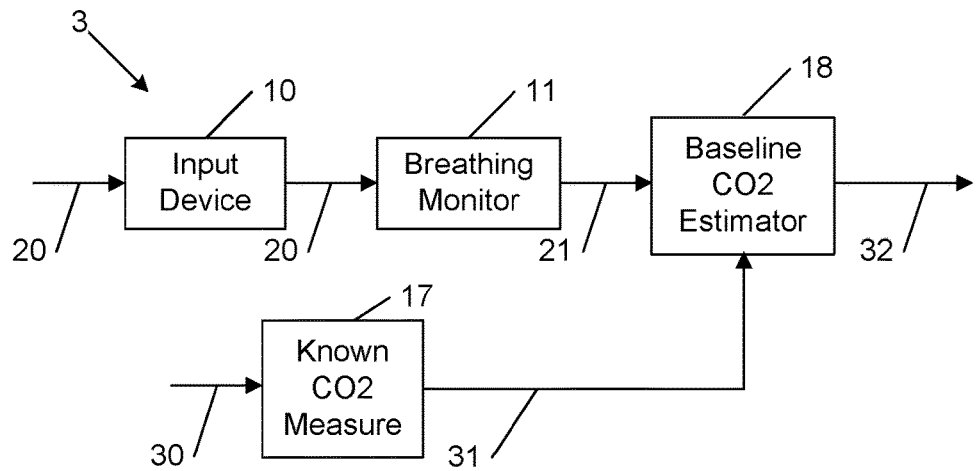
FIG. 5 shows a schematic diagram of a third embodiment of a device according to the present invention.

FIG. 5 shows a schematic diagram of a third embodiment of a device 3 according to the present invention. The device 3 may be used to obtain a baseline or baseline model 32 for the subject's breathing rate changes due to $CO_2$ level changes. The baseline or baseline model 32 can be determined at predetermined or irregular intervals, e.g. every year or every month and may then be used by the device to determine the actual $CO_2$ level. Also, the baseline may be may be obtained by performing measurements for an initial period, for example ten to fifteen minutes and taking an average of the measurements as the baseline. The average could be an arithmetic mean, a median or a modal value. It is better that the initial period occur close to when the people enter the monitored space after it has been un- or lightly occupied for a while since the $CO_2$ levels should, in theory, be close to the natural background levels.

In addition to the elements of the device 1 shown in FIG. 1, the device 3 further comprises a signal input 17 for obtaining environmental data, such a known $CO_2$ level conditions in a controlled environment, known $CO_2$ levels and known air quality data. From monitoring the breathing rate using a camera under such conditions monitoring data are obtained at the signal input 10, which are then used by the breathing monitor to determine one or more breathing parameters 21 of the subject and to estimate the baseline or baseline model 32 by the CO2 estimation unit 18. The signal input may also be coupled to a CO2 sensor from which an absolute measurement may be made. Such a sensor could be placed in the space in question or even in the air purifier (where present) or other air conditioning systems.

During actual measurement the baseline or baseline model 32 will be used in the estimation of the CO2 level. In particular, the CO2 level may be estimated and deviations from the baseline or baseline model 32 may be determined.

In another embodiment the device and method can be used to continuously monitor the health state of the subject.

Figure 6:
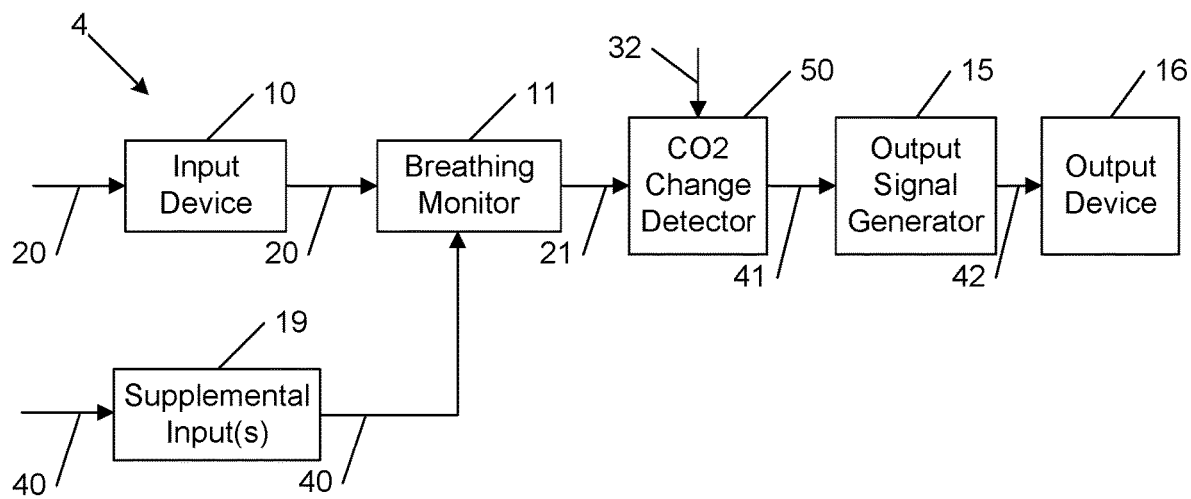
FIG. 6 shows a schematic diagram of a fourth embodiment of a device according to the present invention.

FIG. 6 shows a schematic diagram of a fourth embodiment of a device 4 according to the present invention. In this embodiment the signal input 19 is configured to obtain supplementary data 40 including one or more of air quality data, environmental data, subject behavior data, and sensor data. The breathing monitor 11 identifies changes of the one or more breathing parameters for an individual subject, in particular with respect to a baseline 32, from the obtained one or more monitoring signals 20 and the obtained supplementary data 40.

In another embodiment the breathing rate and heart rate change interaction are exploited. CO2 level changes are generally very well correlated with changes in the respiration parameters, and less with the changes in heart rate. Using this fact, observing an increase in breathing rate with no changes in heart rate, or observing fast changes in breathing rate and slow changes in heart rate can be taken as a sign of increased CO2 level and appropriate actions can be taken to normalize it.

In another embodiment health state monitoring can be performed. Long-term respiration related health condition monitoring, by collecting data over a time frame, and correlating the respiration features to the air quality level present in the car can be used for this purpose. That is, monitoring and changing the air quality through the air purified, and through air purified settings, respiration features, and optionally the car features in a closed loop may be performed. These may be used to generate an overview of health state of the user, and in particular of the diseases or symptom of the user. For example, in one embodiment it may be checked how the air pollution influences the respiration parameters to better evaluate and/or understand the health state of the person.

In another embodiment the user may be coached as mentioned above. Recommendations to the user or to device manufacturers may e.g. be generated. For example, a user can be advised to take a route with a cleaner air, the user/air purifier manufacturer can be advised to replace filter, or to use a particular filter better matching users common routes and destinations, user can be advised to breath in a particular way depending on the air quality at the particular moment (for example, take shallow breaths when air quality is bad, and deeper breaths when better). Further, recommendations can be made to alleviate a particular condition such as asthma, coughing, and dizziness.

Physical exercise can influence the respiration rate. Thus, using the camera, physical exercise could be detected based on motion of the subject's body, and the time interval excluded from CO2 measurement. Physical exercise is known to have a combined effect on respiration rate and heart rate. So in case the heart rate is also measured, the physical exercise could be detected and estimated based on the combined increase in heart rate, and the effect on the respiration rate could be compensated for.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for CO2 monitoring comprising:
   a signal input configured to receive one or more monitoring signals of a monitored area, said monitoring signals being comprised in image data of the monitored area;
   a breathing monitor configured to determine one or more breathing parameters of one or more subjects present in the monitored area from the one or more monitoring signals, and
   a CO2 estimation unit configured to estimate a change in a CO2 level in the monitored area from a change in the determined one or more breathing parameters, wherein an increase in the CO2 level is estimated when a positive change in at least one of breathing rate and breathing volume is detected.

2. The device according to claim 1 wherein the breathing monitor is further configured to establish baseline breathing parameters by obtaining an average breathing rate over an initial period and wherein the CO2 estimation unit estimates the CO2 by comparison of the one or more breathing parameters to said baseline.

3. The device according to claim 1,
   wherein said breathing monitor is configured to separately determine one or more breathing parameters for two or more subjects present in the monitored area and to identify changes of the one or more breathing parameters for the two or more subjects separately and
   wherein said CO2 estimation unit is configured to estimate an absolute CO2 level based on the identified changes of the one or more breathing parameters for the two or more subjects.

4. The device according to claim 1 further comprising
   an output signal generation unit for generating, in dependence on the estimated CO2 level, one or more output signals for controlling an external device and/or for recommending one or more actions to be taken and/or for information, and
   a signal output for outputting the one or more output signals.

5. The device according to claim 4, wherein said output generation unit is configured to generate, as the one or more output signals, one or more of a control signal for controlling or a recommendation to change a setting of a ventilation system, an air purifier, an air condition, one or more openings of a room, or a recommendation to change a location, or change breathing, or minimize physical activity.

6. The device according to claim 1, wherein said breathing monitor is further configured to determine, as the one or more breathing parameters, one or more inspiratory time, expiratory time, inspiration to expiration time ratio, total breath time, fractional inspiration time, variability in the one or more breathing parameters and changes of the one or more breathing parameters over time.

7. The device according to claim 1, wherein said breathing monitor is configured to identify changes of the breathing rate per subject and said $CO_2$ estimation unit is configured to determine, if the breathing rate and/or its change rate exceed a respective threshold for two or more subjects, that the $CO_2$ level has exceeded a $CO_2$ level threshold.

8. The device according to claim 1, wherein said $CO_2$ estimation unit is configured to estimate an absolute $CO_2$ level and/or changes of the $CO_2$ level over time.

9. The device according to claim 1, wherein said signal input is configured to obtain supplementary data including one or more of air quality data, environmental data, subject behavior data, and sensor data,
   wherein said breathing monitor is configured to identify changes of the one or more breathing parameters for an individual subject, in particular with respect to a baseline, from the one or more monitoring signals and the obtained supplementary data.

10. The device according to claim 1, further comprising one or more of
    a heart rate monitor for determining heart rate of the one or more subjects, wherein the $CO_2$ estimation unit is configured to estimate the $CO_2$ level in the monitored area based on the determined one or more breathing parameters and the determined heart rate and/or changes of heart rate over time, and
    a motion detector for detecting physical motion of a subject, wherein said $CO_2$ estimation unit is configured to ignore the one or more breathing parameters of a subject determined during a phase of physical motion of said subject above a motion threshold or take said physical motion into account in the estimation of the $CO_2$ level.

11. A system for $CO_2$ monitoring comprising:
    a monitoring unit for acquiring one or more monitoring signals of a monitored area, and
    a device of claim 1.

12. Vehicle comprising a device according to claim 1 for outputting one or more output signals for controlling a device of the vehicle and/or for recommending one or more actions to be taken.

13. A method according to $CO_2$ monitoring comprising:
    obtaining one or more monitoring signals of a monitored area, said monitoring signals being comprised in image data of the monitored area;
    determining one or more breathing parameters of one or more subjects present in the monitored area from the obtained one or more monitoring signals, and
    estimating a change in a $CO_2$ level in the monitored area from a change in the determined one or more breathing parameters, wherein estimating an increase in the $CO_2$ level comprises observing a positive change in at least one of breathing rate and breathing volume.

14. A computer program product comprising program code stored in a non-transitory media, wherein the computer code is arranged to perform the method of claim 13 when said computer program is carried out on the computer.

\* \* \* \* \*